(12) United States Patent
Herrmann et al.

(10) Patent No.: US 6,476,260 B1
(45) Date of Patent: Nov. 5, 2002

(54) METHOD OF PRODUCING ALDEHYDES AND CARBOXYLIC ACIDS BY OXIDIZING PRIMARY ALCOHOLS

(75) Inventors: Albert Thomas Herrmann, Brunsbüttel (DE); Ernst Tönsen, Brunsbüttel (DE)

(73) Assignee: RWE-DEA Aktiengesellschaft fur Mineraloel und Chemie, Hamburg (DE)

( * ) Notice: Subject to any disclaimer, the term of this patent is extended or adjusted under 35 U.S.C. 154(b) by 0 days.

(21) Appl. No.: 09/509,640

(22) PCT Filed: Sep. 26, 1998

(86) PCT No.: PCT/DE98/02917

§ 371 (c)(1),
(2), (4) Date: May 31, 2000

(87) PCT Pub. No.: WO99/18058

PCT Pub. Date: Apr. 15, 1999

(30) Foreign Application Priority Data

Oct. 2, 1997 (DE) .......................... 197 43 621

(51) Int. Cl.[7] .................. C07C 51/235; C07C 51/16; C07C 45/00
(52) U.S. Cl. .................. 562/538; 562/534; 568/471
(58) Field of Search .................. 568/471; 562/538, 562/534

(56) References Cited

U.S. PATENT DOCUMENTS

| | | |
|---|---|---|
| 4,996,007 A | 2/1991 | Chao et al. |
| 5,094,990 A * | 3/1992 | Sasaki et al. |
| 5,274,187 A * | 12/1993 | Kimura et al. |

FOREIGN PATENT DOCUMENTS

| | | | |
|---|---|---|---|
| EP | 0112261 | * | 6/1984 |
| JP | 62265243 | | 11/1987 |

OTHER PUBLICATIONS

Oxidation of ethanol on platinum–alumina catalysts modified with adsorbed bismuth and gold, Sep. 15, 1986, Ismagilov et al, Chemical Abstracts vol. 105, No. 11 p. 578.*

Chemical Abstracts, vol. 105, No. 11: Ismagilov, Z.R., et al., Oxidation of Ethanol on Platinum–Alumina Catalysts Modified with Adsorbed Bismuth and Gold, Oxid. Commun., 1985.

Chemical Abstracts, vol. 123, No. 9: T. Mallat, et al., Selective Oxidation of Cinnamyl Alcohol to Cinnamaldehyde with Air over Bi–Pt/Alumina Catalysts, J. Catal., 1995.

V. A. Behr, et al., Synthesis of Branched Fatty Acids by Catalytic Oxidation of Alcohols, Fat. Sci. Technol. 94, 1992, pp. 13–18.

* cited by examiner

*Primary Examiner*—Paul J. Killos
*Assistant Examiner*—Robert W. Deemie
(74) *Attorney, Agent, or Firm*—Browning Bushman

(57) ABSTRACT

The invention relates to a method for oxidizing primary alcohols in order to obtain aldehydes and/or carboxylic acids. The reaction takes place in the presence of a catalyst supported on aluminium oxides or aluminium silicates and containing palladium, platinum, cobalt, rhodium, ruthenium, iridium, rhenium, optionally with co-catalysts.

9 Claims, 1 Drawing Sheet

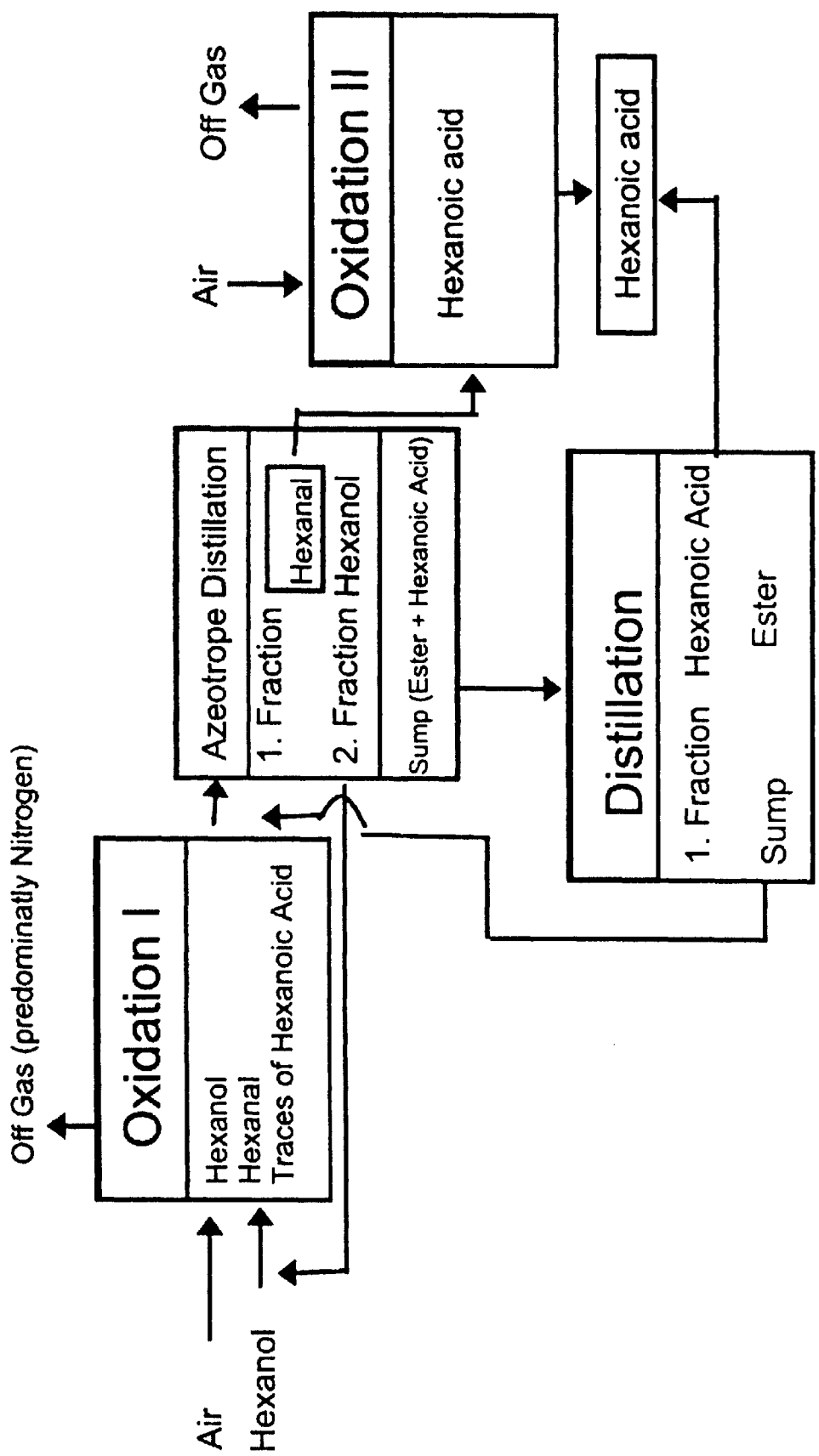

METHOD OF PRODUCING ALDEHYDES AND CARBOXYLIC ACIDS BY OXIDIZING PRIMARY ALCOHOLS

BACKGROUND OF THE INVENTION

1. Field of the Invention

The object of this invention is a method of oxidation of alcohols in the presence of a supported catalyst containing one or more noble metals and one element of group V of the periodic system as a cocatalyst.

2. Description of the Prior Art

It is known that primary alcohols can be oxidized by oxygen as an oxidizing agent according to the following reaction scheme on copper/copper oxide catalysts:

$$RCH_2OH + \tfrac{1}{2}O_2 \rightarrow RCHO + H_2O$$

and this method is used extensively in the industry. Numerous other catalysts/catalyst systems are also known. Silver and Iron-molybdenum mixed oxides which have gained industrial importance as catalysts should also be mentioned here.

Use of ruthenium supported on $Al_2O_3$ for oxidation of primary alcohols is known from U.S. Pat. No. 4,996,007. However, this requires the simultaneous use of oxygen activators such as naphthaquinones or anthraquinones in the presence of solvents such as dichloromethane.

In U.S. Pat. No. 5,274,187, supported catalysts containing platinum, palladium, rhodium, ruthenium, gold, silver and/or copper are used for oxidation of polyhydroxy alcohols. These catalysts may be used in the presence of cocatalysts such as tin, lead, antimony, bismuth, selenium and tellurium. Known supports include carbon, silicates, aluminum oxide, aluminuln silicates, zeolites, molecular sieves and asbestos. The only compounds used as educts are those having at least two hydroxyl groups, at least one of which is a primary hydroxyl group and one is a secondary hydroxyl group.

Oxidation of primary alcohols (without another secondary hydroxyl group) by palladium or platinum catalysts supported on aluminum oxide or aluminum silicates in the presence of atmospheric oxygen without oxygen activators is either not known in the technical world or such catalyst systems are described as inactive (Fat Sci. Tech. 15 (94) 1992).

Furthermore, methods are known in the literature describing the oxidation of primary alcohols in the presence of solvents.

In EP-A1-0112 261 the oxidation of primary alcohols with oxygen using supported binary catalysts containing one of the noble metals of group VIII and bismuth, cadmium, mercury, indium, tellurium, tin, silver and their derivatives in the presence of polar or apolar organic solvents is disclosed. As a supporting agent in particular, carbon is named.

T. Mallar et al. ("Selective Oxidation of Cinnamyl Alcohol to Cinemalaldehyde with Air over Bi—Pt/Alumina Catalysts," in *J. Cat.* 153, pp. 131–143 (1995)) describes the oxidation of a primary unsaturated alcohol to the aldehyde over Bi-Pt/alumina catalysts exemplified by the oxidation of cinnamyl alcohol to cinemalaldehyde. The reaction is always carried out in the presence of water used as a solvent.

The object of JP 62-265243-A is the oxidation of a diol preferably in the presence of water as a solvent containing secondary hydroxyl groups only.

Furthermore, methods are known in the literature describing the oxidation of primary alcohols in the presence of solvents.

In EP-A1-0112 261 the oxidation of primary alcohols with oxygen using supported binary catalysts containing one of the noble metals of group VIII and bismuth, cadmium, mercury, indium, tellurium, tin, silver and their derivatives in the presence of polar or apolar organic solvents is disclosed. As supporting agent in particular carbon is named.

T. Mallar et al. (<< Selective Oxidation of cinnamyl alcohol to cincmalaldehyde with air over Bi—Pt/ Aluwina catalysts" in J. Cat. 153, S. 131–143 (1995)) describes the oxidation of a primary unsaturated alcohol to the aldehyde over Bi—Pt/Alumina catalysts exemplified by the oxidation of cinnamyl alcohol to cinemalaldehyd. The reaction is always carried out in the presence of water used as solvent.

The Object of TP 62-265243-A is the oxidation of a diol preferably in the presence of water as solvent containing secondary hydroxyl-groups only.

The object of the present invention is to make available a highly specific catalyst system which permits oxidation of primary alcohols, preferably long-chain primary alcohols, which need not contain any other activating groups, by atmospheric oxygen in liquid phase at low temperatures and pressures, while at the same time overcoming the disadvantages known from the state of the art such as the use of high temperatures, pressures, oxygen activators, alkali, acid or solvents.

This object is surprisingly achieved by a method of oxidizing primary alcohols containing 4 to 32 carbon atoms and are liquid at the reaction temperature and in which a catalyst containing (a) palladium, platinum, cobalt, rhodium, ruthenium, iridium, rhenium and/or osmium, preferably palladium, platinum, cobalt and/or ruthenium, especially palladium and/or platinum, is brought in contact with the primary alcohols in the presence of a cocatalyst containing (b) bismuth, antimony, arsenic and/or phosphorus, preferably bismuth and/or antimony, especially bismuth, supported on (c) aluminum oxides and/or aluminum silicates is brought into contact with the primary alcohol at a reaction temperature of 20° C. to 130° C. in the absence of solvents and in the presence of molecular oxygen ($O_2$).

The metals used according to this invention may of course also be in the form of compounds, especially in the form of their oxides. The catalysts used according to this invention are also active in the presence of water. The catalysts used according to this invention are advantageously activated before the start of oxidation without oxygen in the presence of the alcohol.

In addition, the reaction is preferably carried out continuously, and the primary alcohol is brought in contact with the catalyst repeatedly. Preferably molecular oxygen is used as the oxidizing agent, and for cost reasons it is used as a mixture in the form of atmospheric oxygen.

Preferred educts are primary alcohols with 4 to 32 carbon atoms, especially 4 to 16 carbon atoms, with the number of carbons preferably amounting to 8 to 32, especially 8 to 20, when an alcohol with a branch in position 2 is used as the primary alcohol.

The oxidation reaction is advantageously carried out in a fixed-bed reactor. The space velocity and residence time depend greatly on the reactor design, but a space velocity of 0.5 to 10 $h^{-1}$ and a residence time of one to ten minutes are generally set.

According to another embodiment of this method, the primary alcohol is oxidized to the aldehyde state in a first reaction, preferably keeping the conversion of the primary alcohol to the aldehyde at less than 40% for each contact (pass) and also preferably eliminating/removing the aldehyde by distillation.

Azeotropic distillation is preferably performed downstream from the oxidation to the aldehydes according to the present invention. In addition to the water formed in the reaction, preferably more water is added to the mixture for azeotropic distillation. At the same time, the excess water also prevents unwanted degradation reactions and side reactions (cleavage of water, formation of acetal and esterification are equilibrium reactions). In addition, the mixture is preferably acidified during azeotropic distillation or distillation is performed in the presence of acid ion exchangers.

Many aldehydes form an azeotrope with water. For example, hexanal and water form an azeotrope that boils at 91° C. Hexanol and hexanoic acid likewise form azeotropes with water, which boil at 97.8° C. and 99.9° C., respectively. Despite the fact that the boiling points are close together, the distillation process is surprisingly free of problems. Pure fractions of alcohol and aldehyde can be collected.

By adding water, the acetal formed during distillation can completely be cleaved to the educts aldehyde and alcohol. Only free hexanoic acid and ester remain in the bottom product (approximately 70%/30% in the case of oxidation of hexanol). These substances can be further separated by distillation, with the ester decomposing into alcohol and acid due to the addition of acid.

FIG. 1/1 gives one possible scheme for the method on the example of oxidation of hexanol.

It is also advantageous to conduct the reaction in such a way that oxidation of the aldehydes obtained in the first reaction to the corresponding carboxylic acids is carried out in a second reaction step without a catalyst under the influence of temperature and molecular oxygen.

The oxidation of aldehydes to carboxylic acids with atmospheric oxygen and without using catalysts is known per se. If the oxidation of the aldehydes is to be accelerated or if side reactions and/or degradation reactions occur to a great extent in oxidation, the oxidation can be accelerated by using pressure or adding catalysts. Salts of transition metals such as cobalt, manganese, iron, nickel, silver, cerium or vanadium are catalytically active. It is known that selectivity is improved by the alkali salts of weak acids as well as baritun qalts of metals.

EXPERIMENTAL EXAMPLE

Oxidation of Hexanol

At a temperature of 112° C., 2.4 L/h hexanol (space velocity 4.7 h$^{-1}$) and 210 L air/h were pumped through a tubular reactor at a total pressure of 30 bar abs. The tubular reactor contained 290 g of a catalyst (5% Pt/Bi on Al$_2$O$_3$). A reaction mixture consisting of 7% hexanal, 3% C$_{18}$ acetal and 90% hexanol was obtained.

In a subsequent azeotropic distillation, aldehyde was removed continuously and hexanol was fed back to the reaction.

In this way, an overall conversion of approximately 99% was achieved, with the selectivity for aldehyde likewise amounting to approximately 99%.

What is claimed is:

1. A method of oxidation of primary alcohols, characterized in that primary alcohols containing 4 to 32 carbon atoms in a liquid state are brought in contact with a catalyst containing
   (a) palladium, platinum, cobalt, rhodium, ruthenium, iridium, rhenium and/or osmium and a co-catalyst containing
   (b) bismuth, antimony, arsenic and/or phosphorus and
   (c) aluminum oxides and/or aluminum silicates as the support in the absence of solvents and in the presence of molecular oxygen (O$_2$) at a reaction temperature of 20 to 120° C.

2. A method according to claim 1, characterized in that the primary alcohol is oxidized only to the aldehyde in a first reaction.

3. A method according to claim 1, characterized in that the resulting aldehyde is removed/eliminated by azeotropic distillation in the presence of water.

4. A method according to claim 1, characterized in that the reaction is carried out continuously and the primary alcohol is repeatedly brought in contact with the catalyst.

5. A method according to claim 2, characterized in that the aldehyde is oxidized to the corresponding carboxylic acid in another reaction in the presence of molecular oxygen, preferably atmospheric oxygen.

6. A method according to claim 1, characterized in that the alcohols containing 4 to 16 carbon atoms.

7. A method according to claim 1, characterized in that the alcohols contain 8 to 24 carbon atoms, and with a branch in position 2, are used as the primary alcohols.

8. A method of oxidation of primary alcohols, characterized in that primary alcohols containing 4 to 32 carbon atoms in a liquid state are brought in contact with a catalyst containing
   (a) palladium, platinum, cobalt and/or ruthenium and a co-catalyst containing
   (b) bismuth and/or antimony and
   (c) aluminum oxides and/or aluminum silicates as the support in the absence of solvents and in the presence of molecular oxygen (O$_2$) at a reaction temperature of 20 to 120° C.

9. The method according to claim 7 wherein the alcohols are branched in the 2 position.

* * * * *